US00RE41133E

(19) United States
(12) Reissued Patent
Hermeling et al.

(10) Patent Number: US RE41,133 E
(45) Date of Reissued Patent: Feb. 16, 2010

(54) GLUCAGON-LIKE PEPTIDE-1 CRYSTALS

(75) Inventors: Ronald Norbert Hermeling, Indianapolis, IN (US); James Arthur Hoffmann, Greenwood, IN (US); Chakravarthy N. N. Narasimhan, Carmel, IN (US)

(73) Assignee: Eli Lilly and Company, Indianapolis, IN (US)

(21) Appl. No.: 11/119,500

(22) Filed: Apr. 29, 2005

Related U.S. Patent Documents

Reissue of:
(64) Patent No.: 6,555,521
Issued: Apr. 29, 2003
Appl. No.: 09/997,792
Filed: Nov. 30, 2001

U.S. Applications:

(63) Continuation of application No. 09/209,799, filed on Dec. 11, 1998, now Pat. No. 6,380,357.
(60) Provisional application No. 60/069,728, filed on Dec. 16, 1997.

(51) Int. Cl.
*A61K 38/22* (2006.01)
*C07K 14/575* (2006.01)

(52) U.S. Cl. ..... 514/12; 514/21; 530/324
(58) Field of Classification Search ..... None
See application file for complete search history.

(56) References Cited

U.S. PATENT DOCUMENTS

| | | | | | |
|---|---|---|---|---|---|
| 5,118,666 | A | * | 6/1992 | Habener | 514/12 |
| 5,120,712 | A | * | 6/1992 | Habener | 514/12 |
| 5,512,549 | A | * | 4/1996 | Chen et al. | 514/12 |
| 5,545,618 | A | * | 8/1996 | Buckley et al. | 514/12 |
| 5,705,483 | A | * | 1/1998 | Galloway et al. | 514/12 |
| 5,734,026 | A | * | 3/1998 | Florin-Robertsson et al. | 530/424 |
| 5,780,599 | A | * | 7/1998 | Junker et al. | 530/399 |
| 5,977,071 | A | * | 11/1999 | Galloway et al. | 514/12 |
| 6,284,727 | B1 | * | 9/2001 | Kim et al. | 514/12 |
| 6,380,357 | B2 | * | 4/2002 | Hermeling et al. | 530/324 |

FOREIGN PATENT DOCUMENTS

| | | | | |
|---|---|---|---|---|
| EP | 0619322 | A | * | 10/1994 |
| EP | 0658568 | A | * | 6/1995 |
| EP | 0869135 | A | * | 10/1998 |
| WO | WO 93/25579 | A | * | 12/1993 |
| WO | WO 95/05848 | A | * | 3/1995 |
| WO | WO 96/20005 | A | * | 7/1996 |
| WO | WO 97/15296 | A | * | 5/1997 |
| WO | WO 98/08871 | A | | 3/1998 |
| WO | WO 98/19698 | A | | 5/1998 |
| WO | WO 98/20895 | A | | 5/1998 |

OTHER PUBLICATIONS

Komatsu, R., et al., Diabetes, 38:902–905, 1989.*
Orskov, C., et al., J. Biol. Chem., 264(22):12826–12829, 1989.*
Majsov, S., Int. J. Peptide Protein Res., 40:33–343, 1989.*
Holz, G., et al., Nature, 361:362–365, 1993.*
Orkov, C., Diabetologia, 35:701–711, 1992.
Mentlein, R., et al., Eur. J. Biochem., 214:829–835, 1993.
Nauck, M. A., et al., J. Clin. Invest., 91:301–307, 1993.
Nauck, M. A., et al., Diabetologia, 36:741–744, 1993.
Gutniak, M., et al., N.E.J. Med., 326(20):1316–1322, 1992.
Thorens, B., et al., Diabetes, 42:1219–1225, 1993.
Suzuki, S., et al., Endocrinology, 125:3109–3114, 1990.
Ananthanancayanan, V. V., et al., Mol. Biol. Cell (Supp.), 3, 250A, #1452, 1992.
Epand, R.M., Mol. Pharmacol., 22:105–108, 1982.
Kim, Y., et al., Pharm. Res., 12:1664–1670, The Application of Crystal Soaking Technique to Study the Effect of Zinc and Cresol on Insulinotropin Crystals Grown from a Saline Solution, 1995.
Naslund, E., et al., Drug News Perspect, 11:92–97, 1998.
Naslund, E. et al., Am. J. Clin. Nutr., 68:525–530, 1998.
Flint, A., et al., J. Clin. Invest., 101:515–520, 1998.
Lone Pridal, et al., International Journal of Pharmaceutics, 136:53–59, Absorption of glucagon–like peptide–1 can be protracted by zinc or protamine, 1996.

* cited by examiner

*Primary Examiner*—Jeffrey E Russel
(74) *Attorney, Agent, or Firm*—Andrea M. Castetter; Gregory A. Cox; Mark J. Stewart

(57) ABSTRACT

The invention provides individual tetragonal flat rod shaped or plate-like crystals of glucagon-like peptide-1 related molecules, processes for their preparation, compositions and methods of use. The crystal preparations exhibit extended time action in vivo and are useful for treating diabetes, obesity and related conditions.

14 Claims, No Drawings

GLUCAGON-LIKE PEPTIDE-1 CRYSTALS

Matter enclosed in heavy brackets [ ] appears in the original patent but forms no part of this reissue specification; matter printed in italics indicates the additions made by reissue.

This application is a continuation of U.S. Ser. No. 09/209,799, filed Dec. 11, 1998, now U.S. Pat. No. 6,380,357, which claims the benefit of U.S. Provisional Application Serial No. 60/069,728, filed Dec. 16, 1997.

FIELD OF THE INVENTION

The present invention relates to peptide chemistry as it applies to pharmaceutical research and development. The invention provides individual tetragonal flat rod shaped or plate-like crystals of glucagon-like peptide-1 related molecules, processes for their preparation, compositions and uses for these improved crystal forms.

BACKGROUND OF THE INVENTION

GLF-1, a 37 amino acid peptide naturally formed by proteolysis of the 160 amino acid precursor protein preproglucagon, was first identified in 1987 as an incretin hormone. GLP-1 is secreted by the L-cells of the intestine in response to food ingestion and has been found to stimulate insulin secretion (insulinotropic action) causing glucose uptake by cells which decreases serum glucose levels (see, e g., Mojsov, S., Int. J. Peptide Protein Research, 40:333–343 (1992)). GLP-1 is poorly active. A subsequent endogenous cleavage between the $6^{th}$ and $7^{th}$ position produces a more potent biologically active GLP-1(7-37)OH peptide. Approximately 80% of the GLP-1(7-37)OH so produced is amidated at the C-terminal in conjunction with removal of he terminal glycine residues in the L-cells and is commonly referred to GLP-1(7-36)$NH_2$. Molecules which are reasonably homologous to, or are derived from, or based on these native forms will generally be referred to as GLP's in this specification.

The biological effects and metabolic turnover of the free acid, the amide form, and many of the numerous known GLP's are similar and show promise as agents for the treatment of diabetes, obesity, and related conditions, including but not limited to impaired glucose tolerance and insulin resistance. However, many GLP's suffer from extremely short biological half lives, some as short as 3–5 minutes, which makes them unattractive for use as pharmaceutical agents. Presently, the activity of dipeptidyl-peptidase-IV (DPP-IV) is believed to readily inactivate many GLP's and is in part responsible for the very short serum half lives observed. Rapid absorption and clearance following parenteral administration are also factors. Thus, there is a need to find a means for prolonging the action of these promising agents.

One such approach has been to modify these molecules to protect them from in vivo cleavage by DPP-IV. For example, see U.S. Pat. No. 5,512,549. In the insulin arts, it has long been known that extended time action can be achieved by administering crystalline protein formulations into the subcutis which act like depots, paying out soluble protein over time.

Heterogeneous micro crystalline clusters of GLP-1(7-37)OH have been grown from saline solutions and examined after crystal soaking treatment with zinc and/or m-cresol (Kim and Haren, Pharma. Res. Vol. 12 No. 11 (1995)). Also, crude crystalline suspensions of GLP(7-36)$NH_2$ containing needle-like crystals and amorphous precipitation have been prepared from phosphate solutions containing zinc or protamine (Pridal, et. al., International Journal of Pharmaceutics Vol. 136, pp. 53–59 (1996)). Also, EP 0 619 322 A 2 describes the preparation of micro-crystalline forms of GLP-1(7-37)OH by mixing solutions of the protein in pH 7–8.5 buffer with certain combinations of salts and low molecular weight polyethylene glycols (PEG). However, such crystalline clusters and crude suspensions are less than ideal for preparing long acting pharmaceutical formulations of GLP's since they are loosely bound heterogeneous clusters of crystals or amorphous-crystalline suspensions which tend to trap impurities and are otherwise difficult to reproducibly manufacture and administer.

Most unexpectedly it was discovered that single tetragonal flat rod shaped or plate-like crystals Of various GLP's could be reproducibly formed from a mother liquor containing a GLP dissolved in a buffered solution and a $C_{1-3}$ alcohol, or optionally a mono or disaccharide, over a wide range of pH conditions. The resulting single flat rod shaped or plate-like crystals are superior to, and offer significant advantages over, the GLP-1(7-37)OH crystal clusters or crude suspensions known in the art.

The single tetragonal flat rod shaped or plate-like crystals of the present invention are less prone to trap impurities and therefore may be produced to greater yields and administered more reproducibly than the known heterogeneous clusters. The crystal compositions of the present invention are pharmaceutically attractive because they are relatively uniform and remain in suspension for a longer period of time than the crystalline clusters or s amorphous crystalline suspensions which tend to settle rapidly, aggregate or clump together, clog syringe needles and generally exacerbate unpredictable dosing. Most importantly, the crystal compositions of the present invention display extended, uniform, and reproducible pharmacokinetics which can be modulated by adding zinc using conventional crystal soaking techniques or, alternatively, by including zinc in the crystallization solution.

BRIEF SUMMARY OF THE INVENTION

The present invention includes processor for preparing single rod-shaped or plate-like crystals of glucagon-like peptide-1 related molecules (GLP's) which comprises preparing a crystallization solution comprising a purified GLP, a buffering agent containing an alcohol or a mono or di saccharide, and optionally, ammonium sulfate or zinc. In another embodiment the GLP crystals having tetragonal flat rod shaped or plate-like morphology selected from the group consisting of a GLP-1 analog, a GLP-1 derivative, a DPP-IV protected GLP, a GLP-1 peptide analog, or a biosynthetic GLP-1 analog are claimed. The invention also includes substantially homogenous compositions of GLP crystals, pharmaceutical formulations and processes for preparing such formulations, and methods for treating diabetes, obesity and related conditions.

DETAILED DESCRIPTION OF THE INVENTION

By custom in the art, the amino terminus of GLP-1(7-37)OH has been assigned number residue 7 and the carboxy-terminus, number 37. This nomenclature carries over o other GLP's. When not specified, the C-terminal is usually considered to be in the traditional carboxyl from. The amino acid sequence and preparation of GLP-1(7-37)OH is well-known in the art. See U.S. Pat. No. 5,120,712, the teachings of which are herein incorporated by reference. For the convenience of the reader the sequence is provided below.

His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly-COOH (SEQ ID NO:1)

"GLP-1 analog" is defined as a molecule having one or more amino acid substitutions, deletions, inversions, or additions relative to GLP-1(7-37) and may include the d-amino acid forms. Numerous GLP-1 analogs are known in the art and include, but are not limited to, GLP-1(7-34) (SEQ ID NO:6), GLP-1(7-35) (SEQ ID NO:7), GLP-1(7-36)$NH_2$ (SEQ ID NO:8), $Gln^9$-GLP-1(7-37) (SEQ ID NO: 9), d-$Gln^9$-GLP-1(7-37) (SEQ ID NO:10), $Thr^{16}$-$Lys^{18}$-GLP-1 (7-37) (SEQ ID NO:11), and $Lys^{18}$-GLP-1(7-37) (SEQ ID NO:12), $Gly^8$-GLP-1(7-36)$NH_2$ (SEQ ID NO:13), $Gly^8$-GLP-1(7-37)OH (SEQ ID NO: 14), $Val^8$-GLP-1(7-37)OH (SEQ ID NO:5), $Met^8$-GLP-1(7-37)OH (SEQ ID NO:15), acetyl-$Lys^9$-GLP-1(7-37) (SEQ ID NO:16), $Thr^9$-GLP-1(7-37) (SEQ ID NO:17), d-$Thr^9$-GLP-1(7-37) (SEQ ID NO:18), $Asn^9$-GLP-1(7-37) (SEQ ID NO:19), d-$Asn^9$-GLP-1(7-37)(SEQ ID NO:20), $Ser^{22}$-$Arg^{23}$ $Arg^{24}$-$Gln^{26}$-GLP-1 (7-37)(SEQ ID NO:21), $Arg^{23}$-GLP-1(7-37) (SEQ ID NO:22), $Arg^{24}$-GLP-1(7-37) (SEQ ID NO:23), α-methyl-$Ala^8$-GLP-1(7-36)$NH_2$ (SEQ ID NO:24), and $Gly^8$-$Glu^{21}$-GLP-1(7-37)OH (SEQ ID NO:25), and the like.

Other GLP-1 analogs consistent with the present invention are described by the formula:

$R_1$-X-Glu-Gly-Thr-Phe-Thr-Ser-Asp-Val-Ser-Ser-Tyr-Leu-Y-Gly-Gln-Ala-Ala-Lys-Z-Phe-Ile-Ala-Trp-Leu-Val-Lys-Gly-Arg-$R_2$ (SEQ ID NO:2)

wherein: $R_1$ is selected from the group consisting of L-histidine, D-histidine, desamino-histidine, 2-amino-histidine, beta-hydroxy-histidine, homohistidine, alpha-fluoromethyl-histidine, and alpha-methyl-histidine; X is selected from the group consisting of Ala, Gly, Val, Thr, Met, Ile, and alpha-methyl-Ala; Y is selected from the group consisting of Glu, Gln, Ala, Thr, Ser, and Gly; Z is selected from the group consisting of Glu, Gln, Ala, Thr, Ser, and Gly; and $R_2$ is selected from the group consisting of $NH_2$, and Gly-OH.

GLP-1 analogs have also been described in WO 91/11457, and include GLP-1(7-34), GLP-1(7-35), GLP-1(7-36), or GLP-1(7-37), or the amide form thereof, and pharmaceutically-acceptable salts thereof, having at least is one modification selected from the group consisting of:

(a) substitution of glycine, serine, cysteine, threonine, asparagine, glutamine, tyrosine, alanine, valine, isoleucine, leucine, methionine, phenylalanine, arginine, or D-lysine for lysine at position 26 and/or position 34; or substitution of glycine, serine, cysteine, threonine, asparagine, glutamine, tyrosine, alanine, valine, isoleucine, leucine, methionine, phenylalanine, lysine, or a D-arginine for arginine at position 36;

(b) substitution of an oxidation-resistant amino acid for tryptophan at position 31;

(c) substitution of at least one of: tyrosine for valine at position 16; lysine for serine at position 18; aspartic acid for glutamic acid at position 21; serine for glycine at position 22; arginine for glutamine at position 23; arginine for alanine at position 24; and glutamine for lysine at position 26; and (d) substitution of at least one of: glycine, serine, or cysteine for alanine at position 8; aspartic acid, glycine, serine, cysteine, threonine, asparagine, glutamine, tyrosine, alanine, valine, isoleucine, leucine, methionine, or phenylalanine for glutamic acid at position 9; serine, cysteine, threonine, asparagine, glutamine, tyrosine, alanine, valine, isoleucine, leucine, methionine, or phenylalanine for glycine at position 10; and glutamic acid for aspartic acid at position 15; and (e) substitution of glycine, serine, cysteine, threonine, asparagine, glutamine, tyrosine, alanine, valine, isoleucine, leucine, methionine, or phenylalanine, or The D- or N-acylated or alkylated form of histidine for histidine at position 7; wherein, in the substitutions in (a), (b), (d), and (e), the substituted amino acids can optionally be in the D-form and the amino acids substituted at position 7 can optionally be in the N-acylated or N-alkylated form.

A "GLP-1 derivative" is defined as a molecule having the amino acid sequence of GLP-1(7-37) or of a GLP-1 analog, but additionally having chemical modification of one or more of its amino acid side groups, α-carbon atoms, terminal amino group, or terminal carboxylic acid group. A chemical modification includes, but is not limited to, adding chemical moieties, creating new bonds, and removing chemical moieties. Modifications at amino acid side groups include, without limitation, acylation of lysine ε-amino groups, N-alkylation of arginine, histidine, or lysine, alkylation of glutamic or aspartic carboxylic acid groups, and deamidation of glutamine or asparagine. Modifications of the terminal amino include, without limitation, the desamino, N-lower alkyl, N-di-lower alkyl, and N-acyl modifications. Modifications of the terminal carboxy group include, without limitation, the amide, lower alkyl amide, dialkyl amide, and lower alkyl ester modifications. Lower alkyl is $C_1$–$C_4$ alkyl. Furthermore, one or more side groups, or terminal groups, may be protected by protective groups known to the ordinarily-skilled protein chemist. The α-carbon of an amino acid may be mono- or dimethylated.

Other GLP-1 derivatives are claimed in U.S. Pat. No. 5,188,666, which is expressly incorporated by reference. Such molecules are selected from the group consisting of a peptide having the amino acid sequence:

His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-X (SEQ ID NO:3)

and pharmaceutically-acceptable salts thereof, wherein X is selected from the group consisting of Lys-COOH and Lys-Gly-COOH; and a derivative of said peptide, wherein said peptide is selected from the group consisting of: a pharmaceutically-acceptable lower alkyl ester of said peptide; and a pharmaceutically-acceptable amide of said peptide selected from the group consisting of amide, lower alkyl amide, and lower dialkyl amide.

Yet another GLP-1 derivatives consistent for use in the present invention include compounds claimed in U.S. Pat. No. 5,512,549, which is expressly incorporated herein by reference described by the formula:

(SEQ ID NO:4)

$R^1$-Ala-Glu-Gly-Thr-Phe-Thr-Ser-Asp-Val-Ser-Ser-Tyr-Leu-Glu-Gly-Gln-Ala-Ala-Xaa-Glu-Phe-Ile-Ala-Trp-Leu-Val-Lys(-$R^2$)-Gly-Arg-$R^3$ wherein $R^1$ is selected from the group consisting of 4-imidazopropionyl, 4-imidazoacetyl, or 4-imidazo-α, α dimethyl-acetyl; $R^2$ is selected from the group consisting of $C_6$–$C_{10}$ unbranched acyl, or is absent; $R^3$ is selected from the group consisting of Gly-OH or $NH_2$; and, Xaa is Lys or Arg, may be used in present invention.

"DPP-IV protected GLP's" refers to GLP-1 analogs which are resistant to the action of DPP-IV. These include analogs having a modified or d amino acid residue in position 8. These also include biosynthetic GLP-1 analogs having Gly or the 1 amino acid residues Val, Thr, Met, Ser, Cys, or Asp in position 8. Other DPP-IV protected GLP's include des amino $His^7$ derivatives.

"GLP-1 peptide analogs" are defined as GLP-1 analogs or derivatives which exclude acylated forms.

"Biosynthetic GLP-1 analogs" are defined as any GLP-1 analogs or derivatives which contain only naturally occurring amino acid residues and are thus capable of being expressed by living cells, including recombinant cells and organisms.

"Treating" is defined as the management and care of a patient for the purpose of combating the disease, condition, or disorder and includes the administration of a compound of present invention to prevent the onset of the symptoms or complications, alleviating the symptoms or complications, or eliminating the disease, condition, or disorder. Treating diabetes therefore includes the maintenance of physiologically desirable blood glucose levels in patients in need thereof.

The flat rod shaped or plate-like GLP crystals of the present invention, which are prepared using the claimed process, vary in size and shape to some degree. Generally, they range in size from approximately 2–25 microns (μm) by 10–150 μm and are flat, having a depth of approximately 0.5–5 μm. These single crystals form from a single nucleation point and do not appear as multiple spiked star-like clusters known in the art.

Given the sequence information herein disclosed and the state of the art is solid phase protein synthesis, GLP's can be obtained via chemical synthesis. However, it also is possible to obtain some GLP's by enzymatically fragmenting proglucagon mating techniques well known to the artisan. Moreover, well known recombinant DAN techniques may be used to express GLP's consistent with the invention.

The principles of solid phase chemical synthesis of polypeptides are well known to the art and may be found in general texts in the area such as Dugas, H. and Penney, C., Bioorganic Chemistry (1981) Springer-Verlag, New York, pgs. 54–92, Merrifield, J. M., Chem. Soc., 85:2149 (1962), and Stewart and Young, Solid Phase Peptide Synthesis, pp. 24–66, Freeman (San Francisco, 1969).

Likewise, the state of the art in molecular biology provides the ordinarily skilled artisan another means by which GLP's can be obtained. Although GLP's may be produced by solid phase peptide synthesis, recombinant methods, or by fragmenting glucagon, recombinant methods are preferable when producing biosynthetic GLP-1 analogs because higher yields are possible.

For purposes of the present invention, GLP-1 peptide analogs and biosynthetic GLP-1 peptide analogs are preferred. More preferred are the DPP-IV protected GLP's, More highly preferred are biosynthetic GLP-1 peptide analogs. Another preferred group of GLP-1 peptide analogs are those which contain a single amino acid substitution at the 8 position which may include d and modified amino acid residues. More highly preferred biosynthetic GLP-1 peptide analogs are those which contain a single amino acid substitution at the 8 position, more preferably those which contain Gly or the 1 amino acid residues Val, Thr or Met in the 8 position.

The present invention provides a process for producing individual tetragonal rod shaped GLP crystals from a mother liquor. Under low to neutral pH conditions ranging from about pH 6–7, preferably about 6.4±about 0.2, the crystallization solution, or mother liquor, contains a final GLP concentration of about 1–10 mg/ml, preferably 2–7 mg/ml.

A number of conventional buffer solutions containing an alcohol or mono or disaccharide are suitable in the practice of the invention. 10 to 50 mM Tris, ammonium acetate, sodium acetate, or Bis-Tris is preferred. The concentration of alcohol ranges from about 2–15% (v/v), preferably 3–13%. Preferred alcohols are selected from the group containing methanol, ethanol, propanol, or glycerol, ethanol being most preferred.

Optionally, the addition of approximately 1% (v/v) ammonium sulfate to the mother liquor will generally increase the yield of crystals. The skilled artisan will also recognize the benefits of adding a preservative such as sodium azide and other such preservatives to the mother liquor to prevent bacterial growth.

In another embodiment, mono or disaccharides may be substituted for the alcohol in the same ratios on a weight in volume basis. Mono or disaccharides suitable for use in the presently claimed process include trehalose, mannitol, glucose, erythrose, ribose, galactose, fructose, maltose, sucrose, and lactose, though trehalose is preferred.

In yet another embodiment of the present invention, the process may be carried out in a neutral or high pH, zinc-containing environment ranging from about pH 7–10, preferably about pH 7.2–9.7. Under these conditions, the GLP concentration is in the range of approximately 1–20 mg/ml, preferably about 2–10 mg/ml. Total zinc, in a molar ratio to GLP, ranges from about 0.5–1.7, preferably 0.6–1.5.

Under such neutral or high pH conditions with zinc, suitable buffers and salts range in concentration from about 10–100 mM glycine and 0–200 mM NaCl, preferably 40–60 mM glycine and 0–150 mM NaCl. Preferred buffers are glycine, aspartic acid and Tris. The alcohol or sugar conditions are as stated previously.

Once the mother liquor is prepared, it is allowed to stand at approximately 15–37° C., preferably about 18–25° C., for 12–48 hours until crystallization occurs. The crystals may then be transferred or otherwise handled without any noticeable deleterious effects to the crystalline morphology suggesting that such crystals may be stored for prolonged periods without suffering structural damage.

In another embodiment, a pharmaceutical formulation may be prepared by adding pharmaceutically acceptable excipients, carriers, preservatives, and diluents directly to the mother liquor after the crystals have formed. In this embodiment, crystallization and subsequent additions are performed under sterile conditions. Zinc may be added directly to the mother liquor to effect the incorporation of zinc into the crystals. Preservatives may be added to the mother liquor to provide formulations of crystals suitable for multiple injections from the same container. Other excipients, such as antioxidants, buffers, acids and bases for pH adjustments, isotonicity agents and the like, may also be added directly to the mother liquor after the crystals have formed.

In another embodiment, the invention provides homogenous compositions of individual tetragonal flat rod shaped or plate-like crystal of GLP's. Prior to the processes herein disclosed and claimed, such compositions could not be achieved. The compositions of the invention are useful in manufacturing processes and for preparing pharmaceutical formulations having extended time action for the treatment or prevention of diabetes, obesity and related conditions.

The claimed GLP crystals and compositions may optionally be treated with zinc using conventional crystal soaking techniques. By soaking the crystals in about a 0.5 mg/ml solution of zinc, complexes of crystals are formed which serve to extend the time action of the administered GLP.

Also, by varying the zinc concentration, the complex composition can be altered leading to longer or shorter time actions.

As noted the invention provides pharmaceutical formulations, which are comprised of single tetragonal flat rod shaped or plate-like crystal of a GLP, together with one or more pharmaceutically acceptable diluents, carriers, or excipients. The crystals can be formulated for parenteral administration for the therapeutic or prophylactic treatment of diabetes, obesity or related conditions. For example, the crystals of the present invention can be admixed with conventional pharmaceutical carriers and excipients. The formulations comprising the claimed crystals contain from about 0.5 to 50 mg/ml of the active GLP, and more specifically from about 1.0 to 10 mg/ml. Furthermore, the crystals of the present invention may be administered alone or in combination with other antidiabetic agents. For subcutaneous or intramuscular preparations, a sterile formulation of the crystals of the present invention can be administered as a suspension in the original or modified crystallization mother liquor or in a pharmaceutical diluent such as pyrogen-free distilled water, physiological saline, or 5% glucose solution. A suitable formulation of the crystals of the present invention may be prepared and administered as a suspension in an aqueous base or a pharmaceutically acceptable oil base, e.g., an ester of a long-chain fatty acid such as ethyl oleate.

Pharmaceutically acceptable preservatives such as an alkylparaben, particularly methylparaben, ethylparaben, propylparaben, or butylparaben or chlorobutanol, phenol or meta-cresol are preferably added to the formulation to allow multi-dose use.

The formulation may also contain an isotonicity agent, which is an agent that is tolerated physiologically and imparts a suitable toxicity to the formulation to prevent the net flow of water across the cell membrane. Compounds, such as glycerin, are commonly used for such purposes at known concentrations. Other possible isotonicity agents include salts, e.g., NaCl, dextrose, mannitol, and lactose. Glycerin is the preferred isotonicity agent. The concentration of the isotonicity agent is in the range known in the art for parenteral formulations, and for glycerin, is preferably about 16 mg/mL to about 25 mg/mL.

The formulation may also contain a pharmaceutically acceptable buffering agent to control the pH at a desired level. The pH is ideally such as to be acceptable to the patient upon administration, yet one at which the formulation is sufficiently stable, both physically and chemically. Preferably, the pH is controlled from a mildly acidic pH to a mildly basic pH, such as, between about pH 5 and pH 9. More preferably, the pH is between about pH 6 and pH 8. Buffering agents include but are not limited to citrate, acetate, phosphate, Tris, or a basic amino acid, such as, lysine or arginine, which are known to be pharmaceutically acceptable in these pH ranges. Other pharmacologically acceptable buffers for buffering at pH in these ranges are known in the art. The selection and concentration of buffer is well within the skill of the art.

EXAMPLE 1 pH 6.4 with 1.0% Ammonium Sulfate 12.5 mg of chemically synthesized GLP-1(7-37)OH analog having Val substituted for Ala in position 8 (V8-GLP-1) was weighed into a 3.0 ml glass vial and treated with 2.0 ml of 10 mM Tris-HCl, 0.02% $NaN_3$, pH 6.4, to give a clear solution at pH 3.6. The pH of the solution was adjusted to 8.7 with 2N NaOH and these lowered to pH 6.4 with 1N HCl. The solution remained clear during the pH adjustments. The solution was filtered through a 0.22 micron Millex GV13 syringe filter (Millipore, Bedford Mass.) into a new 3.0 ml glass vial. The concentration of the V8-GLP-1 stock solution was 4.76 mg/ml as determined from the absorbance at 280 mn and using an extinction coefficient of 2.015 for a 1.0 mg/ml V8-GLP-1 solution in a 1 cm cell. A 0.25 ml aliquot of this V8-GLP-1 stock solution was transferred to a 2.0 ml glass vial. To this solution was added 0.25 ml of a 10 mM Tris-HCl, 0.02% $NaN_3$, pH 6.4, buffer containing 2.0% $(NH_4)_2SO_4$. The vial was sealed, gently swirled, and then placed at 18° C. After 36 hours crystalline clusters were identified at 200× magnification. For quantitation, a portion of the mother liquor was removed and centrifuged at 16,000×g. The V8-GLP-1 content remaining in the clear supernatant was determined from the absorbance at 280 nm as cited above. The crystalline yield was quantitated by subtracting the V8-GLP-1 level in the supernatant from the V8-GLP-1 level in the starting solution. This sample showed a crystallization yield of 63.9%.

EXAMPLE 2 pH 6.4 with 1% Ethanol and 1.0% Ammonium Sulfate

A 0.25 ml aliquot of the V8-GLP-1 stock solution was transferred to a 2.0 ml glass vial as in Example 1. To this solution was added 0.25 ml of a 10 mM Tris-HCl, 0.02% $NaN_3$, pH 6.4, buffer containing 2.0% $(NH_4)_2SO_4$ and 2.0% ethanol. The solution was then treated and evaluated as in Example 1. This sample generated crystalline clusters and a few single tetragonal crystals. The yield was 73.1%.

EXAMPLE 3 pH 6.4 with 5% Ethanol and 1.0% Ammonium Sulfate

A 0.25 ml aliquot of the V8-GLP-1 stock solution was transferred to a 2.0 ml glass vial as in Example 1. To this solution was added 0.25 ml of a 10 mM Tris-HCl, 0.02% $NaN_3$, pH 6.4, buffer containing 2.0 $(NH_4)_2$ $SO_4$ and 10.0% ethanol. The solution was then treated and evaluated as in Example 1. This sample generated crystalline clusters, single tetragonal crystals, and some rods. The yield was 80.3%.

EXAMPLE 4 pH 6.4 with 10% Ethanol and 1.0% Ammonium Sulfate

A 0.25 ml aliquot of the V8-GLP-1 stock solution was transferred to a 2.0 ml glass vial as in Example 1. To this solution was added 0.25 ml of a 10 mM Tris-HCl, 0.02% $NaN_3$, pH 6.4, buffer containing 2.0% $(NH_4)_2SO_4$ and 20.0% ethanol. The solution was then treated and evaluated as in Example 1. This sample generated single tetragonal crystals and rods. The yield was 81.9%.

EXAMPLE 5 pH 6.4 with 1% Ethanol

A 0.25 ml aliquot of the V8-GLP-1 stock solution was transferred to a 2.0 ml glass vial as in Example 1. To this solution was added 0.25 ml of a 10 mM Tris-HCl, 0.02% $NaN_3$, pH 6.4, buffer containing 2.0% ethanol. The solution was then treated and evaluated as in Example 1. This sample generated a trace of crystal clusters. The yield was 8.8%.

EXAMPLE 6 pH 6.4 with 5% Ethanol

A 0.25 ml aliquot of the V8-GLP-1 stock solution was transferred to a 2.0 ml glass vial as in Example 1. To this solution was added 0.25 ml of a 10 mM Tris-HCl, 0.02% $NaN_3$, pH 6.4, buffer containing 10.0% ethanol. The solution was then treated and evaluated as in Example 1. This sample generated crystal clusters, single tetragonal crystals, and rods. The yield was 39.1%.

EXAMPLE 7 pH 6.4 with 10% Ethanol

A 0.25 ml aliquot of the V8-GLP-1 stock solution was transferred to a 2.0 ml glass vial as in Example 1. To this solution was added 0.25 ml of a 10 mM Tris-HCl, 0.02% $NaN_3$, pH 6.4, buffer containing 20.0% ethanol. The solution was then treated and evaluated as in Example 1. This sample generated single tetragonal crystals and rods. The yield was 55.5%.

EXAMPLE 8

Pharmacokinetics 28 mg of biosynthetic V8-GLP-1 was weighted into a lass vial and dispersed in 4.5 ml of 10 mM $NH_4OAc$ to give a turbid solution with a pH of 5.6. The material was completely solubilized by adjusting the pH to 9.5 with 5N NaOH and remained completely soluble after the pH of the solution was lowered to 6.4 with 2N HCl. This solution was filtered through a 0.22 micron Millex GV13 syringe filter into a new glass vial to give a total volume of 4.3 ml. The concentration of the V8-GLP-1 solution was 5.51 mg/ml as determined from the absorbance at 280 nm of a 20× dilution of the stock solution and using an extinction coefficient of 2.015 for a 1 mg/ml V8-GLP-1 solution in a 1 cm cell. To this solution was added 4.3 ml of a 10 mM $NH_4OAc$, 2.0% $(NH_4)_2SO_4$, 20% ethanol, pH 6.4, precipitant buffer. The vial was sealed, the solution was gently swirled and then placed at 18° C. After 72 hours single tetragonal crystals were identified at 200× magnification. The crystals were removed from the mother liquor by low speed centrifugation and resuspended in a 10 mM $NH_4OAc$, 16 mg/ml glycerin, pH 5.5, buffer (buffer A) to a concentration of about 4.0 mg/ml. A portion of the mother liquor was centrifuged at 16,000×g. The V8-GLP-1 content remaining in the clear supernatent was determined from the absorbance at 280 nm. The crystallization yield was quantitated by subtracting the V8-GLP-1 level in the supernatant from the V8-GLP-1 level in the starting solution. This crystallization gave an 83% yield.

Calculated aliquots of 4.0 mg/ml V8-GLP-1 crystal suspensions prepared in a similar manner as above were transferred to five glass vials and diluted with buffer A to a concentration slightly above the final target concentration of 2.5 mg/ml V8-GLP-1. To the crystalline suspensions were added aliquots of a $ZnCl_2$ stock solution (33.4 mg/ml $Zn^{++}$in buffer A) to make final zinc concentrations after 0.5, 1.0, 1.5, or 2.4 mg/ml zinc. The suspensions were gently swirled and placed at 5° C. for 18 hours. The final V8-GLP-1 concentration in each vial was now at the 2.5 mg/ml target concentration. After 18 hours the crystalline V8-GLP-1 zinc suspensions were transferred to room temperature, passed through a 30 gauge needle, and adjusted to pH 6.0 with 1N NaOH.

A 0.1 mg/ml zinc crystalline V8-GLP-1 suspension was prepared by first treating a 2.5 mg/ml crystal suspension with 0.15 mg/ml zinc in the same manner as described above. After 18 hours at 5° C. the zinc treated crystals were isolated by low speed centrifugation and transferred to buffer B (buffer A containing 0.1 mg/ml zinc). The final V8-GLP-1 concentration of this suspension was adjusted to the 2.5 mg/ml target concentration using buffer B. The suspension was passed through a 30 gauge needle, and the pH increased to 6.0 with 1N NaOH.

The give crystalline V8-GLP-1 zinc suspensions descried above, each at 2.5 mg/ml V8-GLP-1 and containing 0.1, 0.5, 1.0, 1.5, or 2.4 mg/ml zinc were tested in overnight-fasted beagle dogs. Each animal received a single 24 nmole/kg subcutaneous injection of the crystalline V8-GLP-1 zinc suspension at time zero. Arterial blood samples (1.5 ml) were withdrawn from the animals at scheduled times, transferred to tubes pretreated with EDTA and containing 40 ul of Trasylol, and then centrifuged. The plasma portion of each sample was separated and stored at −80° C. until analysis. The plasma concentration of immunoreactive V8-GLP-1 in each sample was measured using a RIA procedure. Table 1 shows the resulting immunoreactive V8-GLP-1 plasma levels over a 24 hour time period for each suspension.

TABLE 1

Immunoreactive V8-GLP-1 Levels (picomolar) in Dog Plasma.

| | 0.1 mg/ml Zinc (n = 5) | | 0.5 mg/ml Zinc (n = 5) | | 1.0 mg/ml Zinc (n = 3) | | 1.5 mg/ml Zinc (n = 5) | | 2.4 mg/ml Zinc (n = 5) | |
|---|---|---|---|---|---|---|---|---|---|---|
| Time (hrs) | V8-GLP-1 (pM) | SEM | V8-GLP-1 (pM) | SEM | V8-GLP-1 (pM) | SEM | V8-GLP-1 (pM) | SEM | V8-GLP-1 (pM) | SEM |
| 0 | 0 | 0 | 0 | 0 | 0 | 0 | 0 | 0 | 0 | 0 |
| 1.5 | nd | nd | 123 | 41 | 27 | 4 | 7 | 5 | 5 | 5 |
| 3.0 | nd | nd | 132 | 38 | 38 | 7 | 40 | 13 | 27 | 21 |
| 4.5 | nd | nd | 196 | 51 | 108 | 41 | 76 | 34 | 83 | 37 |
| 6.0 | 301 | 57 | 264 | 79 | 140 | 55 | 142 | 47 | 143 | 60 |
| 7.5 | nd | nd | 265 | 71 | 184 | 57 | 198 | 61 | 179 | 63 |
| 9.0 | nd | nd | 344 | 94 | 220 | 61 | 252 | 64 | 210 | 66 |
| 10.5 | nd | nd | 302 | 80 | 231 | 78 | 250 | 66 | 225 | 50 |
| 12.0 | nd | nd | 282 | 78 | 236 | 76 | 267 | 60 | 238 | 42 |
| 13.5 | nd | nd | 238 | 54 | 241 | 97 | 286 | 74 | 236 | 38 |
| 15.0 | nd | nd | 263 | 67 | 273 | 118 | 325 | 114 | 246 | 28 |
| 16.5 | nd | nd | 235 | 51 | 234 | 106 | 275 | 77 | 218 | 25 |
| 18.0 | nd | nd | 210 | 47 | 184 | 62 | 254 | 59 | 211 | 23 |

TABLE 1-continued

| | Immunoreactive V8-GLP-1 Levels (picomolar) in Dog Plasma. | | | | | | | | | |
|---|---|---|---|---|---|---|---|---|---|---|
| | 0.1 mg/ml Zinc (n = 5) | | 0.5 mg/ml Zinc (n = 5) | | 1.0 mg/ml Zinc (n = 3) | | 1.5 mg/ml Zinc (n = 5) | | 2.4 mg/ml Zinc (n = 5) | |
| Time (hrs) | V8-GLP-1 (pM) | SEM | V8-GLP-1 (pM) | SEM | V8-GLP-1 (pM) | SEM | V8-GLP-1 (pM) | SEM | V8-GLP-1 (pM) | SEM |
| 19.5 | nd | nd | 221 | 54 | 209 | 120 | 278 | 57 | 173 | 9 |
| 21.0 | nd | nd | 215 | 54 | 219 | 115 | 301 | 48 | 178 | 13 |
| 22.5 | nd | nd | 224 | 54 | 193 | 72 | 232 | 23 | 167 | 9 |
| 24.0 | 190 | 30 | 210 | 51 | 187 | 72 | 227 | 34 | 166 | 25 |
| 30.0 | nd | nd | nd | nd | nd | nd | nd | nd | 171 | 24 |

SEM = Standard Error of Mean.
nd = not determined

EXAMPLE 9 pH 9.4 with 5% Trehalose and Zinc 6.8 mg of lyophilized biosynthetic V8-GLP-1 was weighed into a 3.0 ml glass vial. Then, 1.0 ml of a 25 mM glycine-HCl, 150 mM NaCl, 5% trehalose, pH 9.0, buffer was added to dissolve the peptide. The solution was then adjusted to pH 10.3 with 5N NaOH. While the solution was gently stirred 9.0 ul of a 10 mg/ml zinc chloride solution in water was added and the pH adjusted to 9.4 with 2N HCl. The final concentration of V8-GLP-1 was 5.4 mg/ml as determined from the absorbance at 280 nm of a 10× dilution of the solution. The solution was then filtered with a 0.22 micron Millex GV13 syringe filter. The vial was capped, gently swirled, and then placed at ambient temperature. After 24 hours V8-GLP-1 crystal clusters and single rectangular crystals were identified at 430× magnification and estimated to be about 40 microns long, 15 microns wide, and 3 microns thick. A portion of the mother liquor was removed and centrifuged at 16,000×g. The V8-GLP-1 content remaining in the clear supernatant was determined from the absorbance at 280 nm. The crystalline yield was quantitated by subtracting the V8-GLP-1 level in the supernatant from the V8-GLP-1 level in the starting solution. This sample showed a crystallization yield of 89.8%. The small rectangular crystal morphology was not observed in parallel crystallization trials without trehalose.

EXAMPLE 10 pH 9.4 with 10% Mannitol and Zinc 6.8 mg of lyophilized biosynthetic V8-GLP-1 was weighed into a 3.0 ml glass vial, treated with 1.0 ml of a 25 mM glycine-HCl, 150 mM NaCl, 10% mannitol, pH 9.0, buffer and dispersed to give a clear solution. The solution was then adjusted to pH 10.3 with 5N NaOH. While the solution was gently stirred 9.0 ul of 10 mg/ml zinc chloride solution in water was added and the pH adjusted to 9.4 with 2N HCl. The final concentration of V8-GLP-1 was 5.31 mg/ml as determined from the absorbance at 280 nm of a 10× dilution of the crystallization solution. The solution was then filtered with a 0.22 micron Millex GV13 syringe filter. The vial was capped, gently swirled, and then placed at ambient temperature. After 24 hours, small rectangular plate-like crystals of V8-GLP-1 were identified at 430× magnification and estimated to be about 10 to 30 microns long and 10 microns wide. The yield was determined as in Example 9. This sample showed a crystallization yield of 35%.

EXAMPLE 11 pH 9.0 with Zinc

A 1-ml aliquot of a solution of V8-GLP-1 at 3 mg/ml in 50 mM glycine-150 mM NaCl buffer at pH 9.0 was prepared. To this solution was added 7.5 μl of a 20.85 g/ml zinc chloride solution in water, followed by a pH adjustment back up to pH 9.0. After gentle swirling, the clear sample in a 3-ml glass vial was stored at ambient temperature for one day. After this time the crystalline precipitate was examined under the microscope at 90× magnification, revealing clusters of small plates. For quantitation of crystallization yield, the entire suspension as passed through a 0.2 μm filter (Gelman Sciences, Ann Arbor, Michigan). The V8-GLP-1 content remaining in the clear filtrate was quantitated by spectroscopic evaluation at a wavelength of 280 nm, using an extinction coefficient of 2.015 for a 1 mg/ml solution of V8-GLP-1 in a 1 cm cell. The crystallization yield was quantitated by subtracting the V8-GLP-1 level in the supernatant from the V8-GLP-1 level in the starting solution. This sample showed a crystallization yield of 5.6%.

EXAMPLE 12 pH 9.0 with 10% Ethanol and Zinc

A 1-ml aliquot of a solution of V8-GLP-1 was prepared as in Example 11, except that 110 μl of absolute ethanol was added to the solution prior to the addition of the zinc chloride solution. This sample generated large tetragonal crystals, with some clusters, in 80.6% yield.

EXAMPLE 13 pH 9.5 with 10% Ethanol and Zinc

A solution of V8-GLP-1 at 10 mg/ml in 50 mM glycine-150 mM NaCl buffer at pH 10.5 was passed through a sterile. 0.2 μm Acrodisc filter (Gelman Sciences, Ann Arbor, Mich.). To 500 μl of this solution was added 500 μl of a 50 mM glycine-150 mM NaCl buffer at pH 9.0. To this solution was then added 110 μl of absolute ethanol followed y 7.5 μl of a 20.85 mg/ml zinc chloride solution in water. Small additions of 1N HCl was used to adjust the solution to pH 9.5. After gentle swirling the final solution was enclosed in a 3-ml glass vial and stored at ambient temperature for two days. Individual crystalline plates of V8-GLP-1 up to 150 μm in length, approximately 25 μm wide and less than 5 μm thick were generated in 72% yield.

EXAMPLE 14 pH 7.9 with 8.5% Ethanol and Zinc

V8-GLP-1 was prepared at 4 mg/ml in 50 mM glycine pH 9.5 buffer, followed by passage through a 0.2 μm filter (Gelman Sciences, Ann Arbor, Michigan). To 1-ml of this solution was added 100 μl of absolute ethanol and then 60 μl of 2.08 mg/ml zinc chloride solution in water. Small additions of 0.1N HCl were used to adjust the solution to pH 8.0. After gentle swirling the final solution was enclosed in a 3-ml glass vial and stored at ambient temperature for two hours. The pH of the clear solution was then adjusted to pH 7.86 with small additions of 0.1N HCl and storage at ambient temperature continued for two days. Microscopic examination revealed modest-sized, individual tetragonal plates and some clusters. The V8-GLP-1 content remaining in the clear supernatant was quantitated by spectroscopic evaluation at a wavelength of 280 nm, using an extinction coefficient of 2.015 for a 1 mg/ml solution of V8-GLP-1 in a 1 cm cell. The crystallization yield was quantitated by subtracting the V8-GLP-1 level in the supernatant from the V8-GLP-1 level in the starting solution. This sample showed a crystallization yield of 92.2%.

EXAMPLE 15 pH 8.3 with 10% Ethanol and Zinc

V8-GLP-1 was prepared at 7 mg/ml in 100 mM glycine pH 10.5 buffer, followed by passage through a 0.2 μm filter (Gelman Sciences, Ann Arbor, Mich.). To 0.5 ml of this solution was added 0.4 ml of water. Then 100 μl of absolute ethanol was added, followed by about 6 μl of a 20.86 mg/ml zinc chloride solution in water. Small additions of 1N HCl were used to adjust the solution to pH 8.33. After gentle swirling the final solution was enclosed in a 3-ml glass vial and stored at ambient temperature for one day. Microscopic examination revealed small, individual tetragonal plates and some clusters. The V8-GLP-1 content remaining in the clear supernatant was quantitated by spectroscopic evaluation at a wavelength of 280 nm, using an extinction coefficient of 2.015 for a 1 mg/ml solution of V8-GLP-1 in a 1 cm cell. The crystallization yield was quantitated by subtracting the V8-GLP-1 level in the supernatant from the V8-GLP-1 level in the starting solution. This sample showed a crystallization yield of 92.4%.

EXAMPLE 16 pH 7.4 with 8.6% Ethanol and Zinc

V8-GLP-1 was prepared at 4 mg/ml in 50 mM glycine pH 9.0 buffer, followed by passage through a 0.2 μm filter (Gelman Sciences, Ann Arbor, Mich.). To 5 ml of this solution was added 500 μl of absolute ethanol followed by 300 μl of a 2.08 mg/ml zinc chloride solution in water. Small additions of 1N HCl were used to adjust the solution to pH 7.40. After gentle swirling the final solution was enclosed in a 10-ml glass vial and stored at ambient temperature for two days. Microscopic examination revealed modest-sized, individual tetragonal crystals. The V8-GLP-1 constant remaining in the clear supernatant was quantitated by spectroscopic evaluation at a wavelength of 280 nm, using an extinction coefficient of 2.015 for a 1 mg/ml solution of V8-GLP-1 in a 1 cm cell. The crystallization yield was quantitated by subtracting the V8-GLP-1 level in the supernatant from the V8-GLP-1 level in the starting solution. This sample showed a crystallization yield of 85.0%.

EXAMPLE 17 pH 6.4 with 5% Ethanol and 1.0% Ammonium Sulfate

20 V8-GLP-1 (12.5 mg) was weighed into a 20 ml glass vial. 2.0 ml of a 10 mM ammonium acetate buffer containing 150 mM NaCl at pH 6.4 was added. The pH of the turbid solution was clarified by adjustment to pH 9.5 with 5N NaOH, then lowered to pH 6.4 with 2N HCl. The clear solution was filtered through a 0.22 μm Millex GV 13 syringe filter (Millipore, Bedford, Mass.) into a new 20 ml glass vial. The concentration of the V8-GLP-1 stock solution was determined from the absorbance at 280 nm using an extinction coefficient of 2.015 for a 1.0 mg/ml solution of V8-GLP-1 in a 1 cm cell. The protein concentration was adjusted to 5.0 g/ml. A pH 6.4 precipitant solution containing 10 mM ammonium acetate, 150 mM NaCl, 2% ammonium sulfate and 10% ethanol was prepared and filtered through a 0.22 μm Millex GV13 syringe filter. 2 ml of the precipitant solution was slowly added to 2 ml of the V8-GLP-1 stock solution in a glass vial. The vial was gently swirled and incubated at room temperature for 2 days. Tetragonal plate-shaped crystals were observed with a yield of 92%.

The pH of the crystal suspension was adjusted to pH 5.5 with 1N HCl and zinc chloride was added to a final concentration of 0.15 mg/ml. After zinc soaking overnight at room temperature, the pH of the suspension was adjusted to pH 7.5 with 1N NaOH and the preservative meta-cresol was added to a concentration of 3.16 mg/ml. This example shows that, if desired, preserved formulations of GLP-1 crystals can be prepared directly for pharmaceutical use without isolation of the crystals by centrifugation or filtration in an intermediate step.

EXAMPLE 18 pH 7.6 with 8.5% Ethanol and Zinc

V8-GLP-1 was prepared at 4 mg/ml in 50 mM glycine pH 9.0 buffer, followed by passage through a 0.2 μm filter (Acrodisc from Gelman Sciences, Ann Arbor, Mich.). To 10 ml of this solution was added 1 ml of absolute ethanol followed by 600 μl of a 6.7 mg/ml zinc acetate (2-hydrate) solution in water. 100 μl of 2% acetic acid was added, resulting in a pH of about 7.6. After gentle swirling the final solution was enclosed in a 20-ml glass vial and stored at ambient temperature for 24 hours. Microscopic examination revealed modest-sized, individual tetragonal crystals. To the entire solution was then added 3.555 ml of solution containing 3.5 ml of a 14 mg/ml solution of m-cresol in water and 55 μl of 2% acetic acid, resulting in a suspension with a final pH of about 7.2. After gentle swirling the suspension was enclosed in a 20-ml glass vial and stored at ambient temperature for 24 hours. Microscopic examination again revealed modest-sized, individual tetragonal crystals.

After centrifugation of an aliquot for 5 minutes at ambient temperature, the V8-GLP-1 content remaining in the clear supernatant was determined by HPLC analysis of a diluted sample compared to HPLC analysis of V8-GLP-1 standard solution. The crystallization yield was quantitated by subtracting the V8-GLP-1 level in the supernatant from the V8-GLP-1 level in the starting solution. This preserved v8-GLP-1 formulation showed a crystallization yield of 97.7%.

EXAMPLE 19

Crystal Stability

Single tetragonal crystals of V8-GLP-1 were prepared in 10 mM $NH_4OAc$, 1% $(NH_4)_2SO_4$, 10% ethanol buffer at pH 6.4 at 18° C. as described in Example 8. The crystals were removed from the mother liquor by low speed centrifugation and resuspended in a 10 mM $NH_4OAc$, 16 mg/ml glycerin, pH 5.5, buffer to a concentration of about 4.9 mg/ml of V8-GLP-1.

2 ml of this suspension was low speed centrifuged and the supernatant was removed by pipette. The pellet was resuspended in 4 ml of a 10 mM ammonium acetate, 16 mg/ml glycerin pH 5.5 buffer containing 0.1 mg/ml zinc. This crystal suspension was allowed to soak in the zinc solution overnight at 4° C.

The zinc-soaked crystal suspension was divided into four 1-ml aliquots. These suspensions were low speed centrifuged and their supernatants were removed by pipette. Four crystal suspensions were prepared in 10 mM ammonium acetate, 16 mg/ml glycerin, 0.1 mg/ml zinc buffer at pH 6.0. Further pH adjustments to pH 7.4 with 0.1N NaOH and/or additions of meta-cresol to a final concentration of 3.16 mg/ml were made to selected samples as illustrated in Table 2. Each suspension was further divided in half for storage at both room temperature (about 22° C.) and at 4° C., providing a total of 8 test samples as shown in Table 2.

After 10 days, the crystal suspensions were examined under the microscope. The suspension filtrates were then evaluated by HPLC to quantitate the soluble V8-GLP-1 in the crystalline suspensions. The HPLC results are reported in Table 2.

TABLE 2

| | | Soluble V8-GLP-1 in Crystal Suspensions after Storage for 10 days | | |
|---|---|---|---|---|
| Sample | pH | Storage Temperature | mg/ml meta-cresol | Soluble V8-GLP-1 by HPLC |
| A | 6.0 | 4° C. | 0 | 0.19% |
| B | 7.4 | 4° C. | 0 | 0.10% |
| C | 6.0 | 4° C. | 3.16 | 0.05% |
| D | 7.4 | 4° C. | 3.16 | 0.06% |
| E | 6.0 | 22° C. | 0 | 0.16% |

TABLE 2-continued

| | | Soluble V8-GLP-1 in Crystal Suspensions after Storage for 10 days | | |
|---|---|---|---|---|
| Sample | pH | Storage Temperature | mg/ml meta-cresol | Soluble V8-GLP-1 by HPLC |
| F | 7.4 | 22° C. | 0 | 0.08% |
| G | 6.0 | 22° C. | 3.16 | 0.03% |
| H | 7.4 | 22° C. | 3.16 | 0.04% |

This experiment showed that less than 0.2% of the 8-GLP-1 peptide became solubilized in either the preserved r non-preserved crystal formulations over a 10-day period.

Microscopically, the crystal suspensions showed less agglomeration or clumping of the single, tetragonal crystals at pH 7.4 than at pH 6.0, and less at 4° C. than at 22° C. The meta-cresol did not seem to have a significant effect on crystal agglomeration. Additional testing showed the presence of more than 3% ethanol in the crystal suspension, either from the original crystallization mother liquor or from subsequent additions, greatly reduced the clumping tendency of the crystals in both preserved and non-preserved formulations. Further tests revealed that, although the crystals are relatively stable in the presence of meta-cresol, they are less stable in the presence of 0.5% phenol, which slowly leads to the formation of amorphous material.

Additional crystal stability tests showed that the V8-GLP-1 crystals prepared at pH 6.4 are very stable chemically, with no degradation peaks observed by HPLC analysis after storage at 5° C. or room temperature for up to two months.

Stability tests of crystals prepared in glycine buffer as described in Example 16 showed the V8-GLP-1 crystals stored in the original mother liquor were not stable when meta-cresol was added to the level of 3.16 mg/ml. This test resulted in dissolution of the crystals after only 1 day. The crystal instability in this composition could be effectively blocked by addition of zinc (via a zinc chloride solution) prior to addition of the preservative.

SEQUENCE LISTING

```
<160> NUMBER OF SEQ ID NOS: 25

<210> SEQ ID NO 1
<211> LENGTH: 31
<212> TYPE: PRT
<213> ORGANISM: Homo sapiens

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30


<210> SEQ ID NO 2
<211> LENGTH: 31
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa at position 1 is L-histidine, D-histidine,
      or a modified residue
```

-continued

<220> FEATURE:
<221> NAME/KEY: MOD_RES
<222> LOCATION: (1)..(1)
<223> OTHER INFORMATION: Xaa at position 1 is desamino-histidine,
2-amino-histidine, beta-hydroxy-histidine, homohistidine,
alpha-fluoromethyl-histidine, or alpha-methyl-histidine
<220> FEATURE:
<221> NAME/KEY: MISC_FEATURE
<222> LOCATION: (2)..(2)
<223> OTHER INFORMATION: Xaa at position 2 is Ala, Gly, Val, Thr, Met,
Ile, or a modified residue
<220> FEATURE:
<221> NAME/KEY: MOD_RES
<222> LOCATION: (2)..(2)
<223> OTHER INFORMATION: Xaa at position 2 is alpha-methyl-Ala
<220> FEATURE:
<221> NAME/KEY: MISC_FEATURE
<222> LOCATION: (15)..(15)
<223> OTHER INFORMATION: Xaa at position 15 is Glu, Gln, Ala, Thr, Ser,
or Gly
<220> FEATURE:
<221> NAME/KEY: MISC_FEATURE
<222> LOCATION: (21)..(21)
<223> OTHER INFORMATION: Xaa at position 21 is Glu, Gln, Ala, Thr, Ser,
or Gly
<220> FEATURE:
<221> NAME/KEY: MOD_RES
<222> LOCATION: (30)..(30)
<223> OTHER INFORMATION: Arg at position 30 is amidated when Xaa at
position 31 is absent
<220> FEATURE:
<221> NAME/KEY: MISC_FEATURE
<222> LOCATION: (31)..(31)
<223> OTHER INFORMATION: Xaa at position 31 is Gly or absent

<400> SEQUENCE: 2

Xaa Xaa Glu Gly Thr Phe Thr Ser Asp Val Ser Ser Tyr Leu Xaa Gly
1 5 10 15

Gln Ala Ala Lys Xaa Phe Ile Ala Trp Leu Val Lys Gly Arg Xaa
20 25 30

<210> SEQ ID NO 3
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (28)..(28)
<223> OTHER INFORMATION: Xaa at position 28 is Lys or absent
<220> FEATURE:
<221> NAME/KEY: MISC_FEATURE
<222> LOCATION: (29)..(29)
<223> OTHER INFORMATION: Xaa at position 29 is absent or is Gly when Xaa
at position 28 is Lys

<400> SEQUENCE: 3

His Ala Glu Gly Thr Phe Thr Ser Asp Val Ser Ser Tyr Leu Glu Gly
1 5 10 15

Gln Ala Ala Lys Glu Phe Ile Ala Trp Leu Val Xaa Xaa
20 25

<210> SEQ ID NO 4
<211> LENGTH: 30
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: The groups of 4-imidazopropionyl, -continued

```
      4-imidazoacetyl, 4-imidazo-alpha, or alpha-dimethyl-acetyl modify
      Ala at position 1
<220> FEATURE:
<221> NAME/KEY: MISC_FEATURE
<222> LOCATION: (19)..(19)
<223> OTHER INFORMATION: Xaa at position 19 is Lys or Arg
<220> FEATURE:
<221> NAME/KEY: MOD_RES
<222> LOCATION: (29)..(29)
<223> OTHER INFORMATION: When position 30 is absent, Arg at position 29
      is amidated as NH2
<220> FEATURE:
<221> NAME/KEY: MISC_FEATURE
<222> LOCATION: (30)..(30)
<223> OTHER INFORMATION: Xaa at position 30 is Gly or is absent, and
      when Gly is absent, Arg at position 29 is amidated as NH2

<400> SEQUENCE: 4

Ala Glu Gly Thr Phe Thr Ser Asp Val Ser Ser Tyr Leu Glu Gly Gln
1               5                   10                  15

Ala Ala Xaa Glu Phe Ile Ala Trp Leu Val Lys Gly Arg Xaa
            20                  25                  30


<210> SEQ ID NO 5
<211> LENGTH: 31
<212> TYPE: PRT
<213> ORGANISM: Artificial Sequence
<220> FEATURE:
<223> OTHER INFORMATION: Synthetic construct

<400> SEQUENCE: 5

His Val Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30


<210> SEQ ID NO 6
<211> LENGTH: 28
<212> TYPE: PRT
<213> ORGANISM: Artificial Sequence
<220> FEATURE:
<223> OTHER INFORMATION: Synthetic construct

<400> SEQUENCE: 6

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys
            20                  25


<210> SEQ ID NO 7
<211> LENGTH: 29
<212> TYPE: PRT
<213> ORGANISM: Artificial Sequence
<220> FEATURE:
<223> OTHER INFORMATION: Synthetic construct

<400> SEQUENCE: 7

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly
            20                  25


<210> SEQ ID NO 8
<211> LENGTH: 30
<212> TYPE: PRT
<213> ORGANISM: Artificial Sequence
<220> FEATURE:
```

-continued

<223> OTHER INFORMATION: Synthetic construct

<400> SEQUENCE: 8

His Ala Glu Gly Thr Phe Thr Ser Asp Val Ser Ser Tyr Leu Glu Gly
1 5 10 15

Gln Ala Ala Lys Glu Phe Ile Ala Trp Leu Val Lys Gly Arg
20 25 30

<210> SEQ ID NO 9
<211> LENGTH: 31
<212> TYPE: PRT
<213> ORGANISM: Artificial Sequence
<220> FEATURE:
<223> OTHER INFORMATION: Synthetic construct

<400> SEQUENCE: 9

His Ala Gln Gly Thr Phe Thr Ser Asp Val Ser Ser Tyr Leu Glu Gly
1 5 10 15

Gln Ala Ala Lys Glu Phe Ile Ala Trp Leu Val Lys Gly Arg Gly
20 25 30

<210> SEQ ID NO 10
<211> LENGTH: 31
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa at position 3 is D-Gln

<400> SEQUENCE: 10

His Ala Xaa Gly Thr Phe Thr Ser Asp Val Ser Ser Tyr Leu Glu Gly
1 5 10 15

Gln Ala Ala Lys Glu Phe Ile Ala Trp Leu Val Lys Gly Arg Gly
20 25 30

<210> SEQ ID NO 11
<211> LENGTH: 31
<212> TYPE: PRT
<213> ORGANISM: Artificial Sequence
<220> FEATURE:
<223> OTHER INFORMATION: Synthetic construct

<400> SEQUENCE: 11

His Ala Glu Gly Thr Phe Thr Ser Asp Thr Ser Lys Tyr Leu Glu Gly
1 5 10 15

Gln Ala Ala Lys Glu Phe Ile Ala Trp Leu Val Lys Gly Arg Gly
20 25 30

<210> SEQ ID NO 12
<211> LENGTH: 31
<212> TYPE: PRT
<213> ORGANISM: Artificial Sequence
<220> FEATURE:
<223> OTHER INFORMATION: Synthetic construct

<400> SEQUENCE: 12

His Ala Glu Gly Thr Phe Thr Ser Asp Val Ser Lys Tyr Leu Glu Gly
1 5 10 15

Gln Ala Ala Lys Glu Phe Ile Ala Trp Leu Val Lys Gly Arg Gly
20 25 30

-continued

<210> SEQ ID NO 13
<211> LENGTH: 30
<212> TYPE: PRT
<213> ORGANISM: Artificial Sequence
<220> FEATURE:
<223> OTHER INFORMATION: Synthetic construct

<400> SEQUENCE: 13

His Gly Glu Gly Thr Phe Thr Ser Asp Val Ser Ser Tyr Leu Glu Gly
1 5 10 15

Gln Ala Ala Lys Glu Phe Ile Ala Trp Leu Val Lys Gly Arg
20 25 30

<210> SEQ ID NO 14
<211> LENGTH: 31
<212> TYPE: PRT
<213> ORGANISM: Artificial Sequence
<220> FEATURE:
<223> OTHER INFORMATION: Synthetic construct

<400> SEQUENCE: 14

His Gly Glu Gly Thr Phe Thr Ser Asp Val Ser Ser Tyr Leu Glu Gly
1 5 10 15

Gln Ala Ala Lys Glu Phe Ile Ala Trp Leu Val Lys Gly Arg Gly
20 25 30

<210> SEQ ID NO 15
<211> LENGTH: 31
<212> TYPE: PRT
<213> ORGANISM: Artificial Sequence
<220> FEATURE:
<223> OTHER INFORMATION: Synthetic construct

<400> SEQUENCE: 15

His Met Glu Gly Thr Phe Thr Ser Asp Val Ser Ser Tyr Leu Glu Gly
1 5 10 15

Gln Ala Ala Lys Glu Phe Ile Ala Trp Leu Val Lys Gly Arg Gly
20 25 30

<210> SEQ ID NO 16
<211> LENGTH: 31
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa at position 3 is acetyl-Lys

<400> SEQUENCE: 16

His Ala Xaa Gly Thr Phe Thr Ser Asp Val Ser Ser Tyr Leu Glu Gly
1 5 10 15

Gln Ala Ala Lys Glu Phe Ile Ala Trp Leu Val Lys Gly Arg Gly
20 25 30

<210> SEQ ID NO 17
<211> LENGTH: 31
<212> TYPE: PRT
<213> ORGANISM: Artificial Sequence
<220> FEATURE:
<223> OTHER INFORMATION: Synthetic construct

<400> SEQUENCE: 17

His Ala Thr Gly Thr Phe Thr Ser Asp Val Ser Ser Tyr Leu Glu Gly
1 5 10 15

Gln Ala Ala Lys Glu Phe Ile Ala Trp Leu Val Lys Gly Arg Gly
20 25 30

<210> SEQ ID NO 18
<211> LENGTH: 31
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa at position 3 is D-Thr

<400> SEQUENCE: 18

His Ala Xaa Gly Thr Phe Thr Ser Asp Val Ser Ser Tyr Leu Glu Gly
1 5 10 15

Gln Ala Ala Lys Glu Phe Ile Ala Trp Leu Val Lys Gly Arg Gly
20 25 30

<210> SEQ ID NO 19
<211> LENGTH: 31
<212> TYPE: PRT
<213> ORGANISM: Artificial Sequence
<220> FEATURE:
<223> OTHER INFORMATION: Synthetic construct

<400> SEQUENCE: 19

His Ala Asn Gly Thr Phe Thr Ser Asp Val Ser Ser Tyr Leu Glu Gly
1 5 10 15

Gln Ala Ala Lys Glu Phe Ile Ala Trp Leu Val Lys Gly Arg Gly
20 25 30

<210> SEQ ID NO 20
<211> LENGTH: 31
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa at position 3 is D-Asn

<400> SEQUENCE: 20

His Ala Xaa Gly Thr Phe Thr Ser Asp Val Ser Ser Tyr Leu Glu Gly
1 5 10 15

Gln Ala Ala Lys Glu Phe Ile Ala Trp Leu Val Lys Gly Arg Gly
20 25 30

<210> SEQ ID NO 21
<211> LENGTH: 31
<212> TYPE: PRT
<213> ORGANISM: Artificial Sequence
<220> FEATURE:
<223> OTHER INFORMATION: Synthetic construct

<400> SEQUENCE: 21

His Ala Glu Gly Thr Phe Thr Ser Asp Val Ser Ser Tyr Leu Glu Ser
1 5 10 15

Arg Arg Ala Gln Glu Phe Ile Ala Trp Leu Val Lys Gly Arg Gly
20 25 30

<210> SEQ ID NO 22
<211> LENGTH: 31

-continued

```
<212> TYPE: PRT
<213> ORGANISM: Artificial Sequence
<220> FEATURE:
<223> OTHER INFORMATION: Synthetic construct

<400> SEQUENCE: 22

His Ala Glu Gly Thr Phe Thr Ser Asp Val Ser Ser Tyr Leu Glu Gly
1               5                   10                  15

Arg Ala Ala Lys Glu Phe Ile Ala Trp Leu Val Lys Gly Arg Gly
            20                  25                  30


<210> SEQ ID NO 23
<211> LENGTH: 31
<212> TYPE: PRT
<213> ORGANISM: Artificial Sequence
<220> FEATURE:
<223> OTHER INFORMATION: Synthetic construct

<400> SEQUENCE: 23

His Ala Glu Gly Thr Phe Thr Ser Asp Val Ser Ser Tyr Leu Glu Gly
1               5                   10                  15

Gln Arg Ala Lys Glu Phe Ile Ala Trp Leu Val Lys Gly Arg Gly
            20                  25                  30


<210> SEQ ID NO 24
<211> LENGTH: 30
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa at position 2 is alpha-methyl-Ala

<400> SEQUENCE: 24

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30


<210> SEQ ID NO 25
<211> LENGTH: 31
<212> TYPE: PRT
<213> ORGANISM: Artificial Sequence
<220> FEATURE:
<223> OTHER INFORMATION: Synthetic construct

<400> SEQUENCE: 25

His Gly Glu Gly Thr Phe Thr Ser Asp Val Ser Ser Tyr Leu Gln Gly
1               5                   10                  15

Gln Ala Ala Lys Glu Phe Ile Ala Trp Leu Val Lys Gly Arg Gly
            20                  25                  30
```

We claim:

1. Crystals comprising zinc, and a GLP-1 analog wherein the crystals have a tetragonal flat rod shaped or plate-like morphology and the GLP-1 analog is a peptide of the formula:

$R_1$-X-Glu-Gly-Thr-Phe-Thr-Ser-Asp-Val-Ser-Ser-Tyr-Leu-Y-Gly-Gln-Ala-Ala-Lys-Z-Phe-Ile-Ala-Trp-Leu-Val-Lys-Gly-Arg-$R_2$ SEQ ID NO:2 wherein: $R_1$ is selected from the group consisting of L-histidine, D-histidine, desamino-histidine, 2-amino-histidine, beta-hydroxy-histidine, homohistidine, alpha-fluoromethyl-histidine, and alpha-methyl-histidine; X is selected from the group consisting of Ala, Gly, Val, Thr, Met, Ile, and alpha-methyl-Ala; Y is selected from the group consisting of Glu, Gln, Ala, Thr, Ser, and Gly; Z is selected from the group consisting of Glu, Gln, Ala, Thr, Ser, and Gly; and $R_2$ is selected from the group consisting of $NH_2$, and Gly-OH.

2. The crystals of claim 1 wherein X is selected from the group consisting of Gly, Val, Thr, Met, Ile, and alpha-methyl-Ala.

3. The crystals of claim 2 having a size from between about 2–25 microns by 10–150 microns with a depth from about 0.5–5 microns.

4. A pharmaceutical formulation comprising crystals as claimed in claim 1 together with one or more pharmaceutical acceptable diluents, carriers, or excipients.

5. A pharmaceutical formulation comprising crystals as claimed in claim 2 with one or more pharmaceutically acceptable diluents, carriers, or excipients.

6. A pharmaceutical formulation comprising crystals as claimed in claim 3 with one or more pharmaceutically acceptable diluents, carriers, or excipients.

*7. Crystals comprising zinc, and a GLP-1 analog wherein the crystals have a tetragonal flat rod shaped or plate-like morphology and the GLP-1 analog has at least one modification selected from the group consisting of:*

(*a*) *substitution of glycine, serine, cysteine, threonine, asparagine, glutamine, tyrosine, alanine, valine, isoleucine, leucine, methionine, phenylalanine, arginine, or D-lysine for lysine at position 26 and/or position 34; or substitution of glycine, serine, cysteine, threonine, asparagine, glutamine, tyrosine, alanine, valine, isoleucine, leucine, methionine, phenylalanine, lysine, or D-arginine for arginine at position 36;*

(*b*) *substitution of an oxidation-resistant amino acid for tryptophan at position 31;*

(*c*) *substitution of at least one of tyrosine for valine at position 16; lysine for serine at position 18; aspartic acid for glutamic acid at position 21; serine for glycine at position 22; arginine for glutamine at position 23; arginine for alanine at position 24; and glutamine for lysine at position 26; and*

(*d*) *substitution comprising at least one of: glycine, serine, or cysteine for alanine at position 8; aspartic acid, glycine, serine, cysteine, threonine, asparagine, glutamine, tyrosine, alanine, valine, isoleucine, leucine, methionine, or phenylalanine for glutamic acid at position 9; serine, cysteine, threonine, asparagine, glutamine, tyrosine, alanine, valine, isoleucine, leucine, methionine, or phenylalanine for glycine at position 10; and glutamic acid for aspartic acid at position 15; and*

(*e*) *substitution of glycine, serine, cysteine, threonine, asparagine, glutamine, tyrosine, alanine, valine, isoleucine, leucine, methionine, or phenylalanine or the D-or N-acylated or alkylated form of histidine for histidine at position 7.*

*8. The crystals of claim 7, wherein the GLP-1 analog comprises an arginine substituted for lysine at position 34.*

*9. The crystals of claim 8, wherein an epsilon-amino group of lysine is acylated.*

*10. The crystals of claim 7 having a size from between about 2-25 microns by 10-150 microns with a depth from about 0.5-5 microns.*

*11. The crystals of claim 8 having a size from between about 2-25 microns by 10-150 microns with a depth from about 0.5-5 microns.*

*12. The crystals of claim 9 having a size from between about 2-25 microns by 10-150 microns with a depth from about 0.5-5 microns.*

*13. A pharmaceutical formulation comprising crystals as claimed in claim 8 with one or more pharmaceutically acceptable diluents, carriers, or excipients.*

*14. A pharmaceutical formulation comprising crystals as claimed in claim 9 with one or more pharmaceutically acceptable diluents, carriers, or excipients.*

* * * * *

UNITED STATES PATENT AND TRADEMARK OFFICE

CERTIFICATE OF CORRECTION

PATENT NO. : RE 41,133 E
APPLICATION NO. : 11/119500
DATED : February 16, 2010
INVENTOR(S) : Ronald Norbert Hermeling et al.

It is certified that error appears in the above-identified patent and that said Letters Patent is hereby corrected as shown below:

Title Pg, Item (75) Inventors: delete "Greenwood," and insert -- Bedford, --

Title Pg, Item (75) Inventors: delete "N.N."

Title Pg, Item (75), Inventors: delete "Carmel, IN (US)" and insert -- Scotch Plains, NJ (US) --

In Column 29, line 5, in Claim 4, delete "pharmaceutical" and insert -- pharmaceutically --

Signed and Sealed this

Twenty-fifth Day of May, 2010

David J. Kappos

David J. Kappos
*Director of the United States Patent and Trademark Office*